United States Patent [19]

Göttfert

[11] Patent Number: 5,959,195
[45] Date of Patent: Sep. 28, 1999

[54] PROCESS FOR DETERMINING AND EVALUATING MELT FLOW INDEX VALUES

[75] Inventor: Axel Göttfert, Buchen, Germany

[73] Assignee: Gottfert Werkstoff-Prufmaschinen GmbH, Buchen, Germany

[21] Appl. No.: 09/043,194

[22] PCT Filed: Sep. 13, 1996

[86] PCT No.: PCT/DE96/01736

§ 371 Date: Mar. 13, 1998

§ 102(e) Date: Mar. 13, 1998

[87] PCT Pub. No.: WO97/10492

PCT Pub. Date: Mar. 20, 1997

[30] Foreign Application Priority Data

Sep. 13, 1995 [DE] Germany ............ 195 33 859

[51] Int. Cl.$^6$ ............ G01N 11/04; G05D 11/00
[52] U.S. Cl. ............ 73/54.11; 137/92
[58] Field of Search ............ 73/54.14, 54.01, 73/54.04, 54.06, 54.07, 54.11; 137/92

[56] References Cited

U.S. PATENT DOCUMENTS

| | | |
|---|---|---|
| 3,048,030 | 8/1962 | De Haven . |
| 3,203,225 | 8/1965 | Sieglaff et al. ............ 73/54.14 |
| 3,252,320 | 5/1966 | Welty . |
| 3,468,158 | 9/1969 | Chien . |
| 3,908,442 | 9/1975 | Chimel . |
| 4,449,395 | 5/1984 | Kurtz et al. . |

FOREIGN PATENT DOCUMENTS

| | | |
|---|---|---|
| 0 406 805 | 1/1991 | European Pat. Off. . |
| 0 595 276 | 5/1994 | European Pat. Off. . |
| WO 92/17764 | 10/1992 | WIPO . |

*Primary Examiner*—Hezron Williams
*Assistant Examiner*—Jay L. Politzer
*Attorney, Agent, or Firm*—Alston & Bird LLP

[57] ABSTRACT

A method is proposed for determining and evaluating melt flow index values (MFR values) of thermoplastic materials with the aid of a continuously operating on-line capillary rheometer. The pressure difference $\Delta p$ between the inlet and the outlet of a measuring nozzle of the capillary rheometer is controlled such that $MFR_{on-line} = MFR_{lab}$, where $MFR_{on-line}$ is the melt flow index value that is determined on line, and $MFR_{lab}$ the melt flow index value that is determined under standardized laboratory conditions.

10 Claims, 5 Drawing Sheets

PROCESS FOR DETERMINING AND EVALUATING MELT FLOW INDEX VALUES

The invention relates to a method of determining and evaluating melt flow index values (MFR values) of thermoplastic materials with the aid of a continuously operating on-line capillary rheometer, wherein a pressure difference Δp is predetermined between an inlet and an outlet of a measuring nozzle of the capillary rheometer.

Based on their wide measuring range and their simple and robust construction, capillary rheometers are rheometer systems most frequently used in the polymer industry.

One possibility of acquiring measurement data with a capillary rheometer consists in measuring the pressure difference between the inlet and the outlet of the measuring nozzle, wherein the volume flow through the measuring nozzle is generally kept constant. However, it is also possible to predetermine a constant pressure difference and to measure the thereby resultant volume flow through the measuring nozzle. In practice, it is common to use round hole nozzles or flat slotted channels as a measuring nozzle. In continuously operating on-line capillary rheometers, the volume flow is metered by means of so-called melt pumps, for example, gear pumps. The adjustable operating range of melt pumps is from 0.5 to 100 rpm. The delivery is normally from 0.6 to 1.3 cm$^3$ per revolution. As a result, a variable volume flow can be predetermined, which makes it possible to cover the viscosity function of the melt within a specifiable range. On the condition of identical nozzle geometries, identical results are obtained with on-line capillary rheometers and conventional laboratory instruments.

From the viewpoint of the industry, the melt flow index (MFR) represents the most popular parameter for describing the flow behavior of thermoplastics. Even when this value is determined within the scope of a classic one-point measurement, it is often specified by raw material producers for application engineering as the only Theological value for product specification. In this respect, central importance is also attributed to the melt flow index (MFR) in the product-concomitant quality control and quality assurance.

According to DIN, ISO, the melt flow index is determined as the extruded test material in grams, which is extruded in ten minutes from a temperature-controlled channel through a defined nozzle, the test material being weighted, via a piston, by a defined load M.

Since in the case of many polymers, the density ζ of the melt does not change significantly, it has been found practical to also standardize the volume index (MVR). In its instance, the extruded material is specified in cubic centimeters. The determination of the volume index (MVR) represents the more common form of determining measurement data.

The measuring nozzle of melt flow indexers as are used in a laboratory has a diameter of 2.1 mm and a length of 8 mm. The load weight is selected from 2.16 kg to 21.6 kg as a function of each polymer being characterized.

Unlike the melt flow indexers used in the laboratory, the measuring nozzles of on-line capillary rheometers have a length to diameter (L/D) ratio greater than 10. This configuration is necessary, for purposes of generating between the inlet and the outlet of the measuring nozzle pressure differences of a magnitude, which can be acquired with the use of commercially available pressure gauges.

The MFR or MVR measurement is in a first approximation a creep test, wherein the shear stress $\tau_W$ that acts upon the melt as a result of the load weight is constant on the wall.

Different nozzle geometries of melt flow indexers used in the laboratory and on-line capillary rheometers, and likewise different flow conditions that are present in each case make it only difficult to draw a comparison between the MFR or MVR values acquired in the laboratory and those acquired on line.

It is therefore the object of the invention to enable a kind of to-scale transfer, so that continuously acquired MFR and MVR values correspond within acceptable limits to MFR or MVR values that are determined under standardized laboratory conditions.

The method of the present invention accomplishes the foregoing object by the step of claim 1. Accordingly, the pressure difference Δp is adjusted within the scope of the initially described method, so that $$MFR_{on-line} = MFR_{lab},$$

where $MFR_{on-line}$ is the melt flow index value acquired on line, and $MFR_{Lab}$ the melt flow index value determined under standardized laboratory conditions.

When simulating the melt flow index measurement in an on-line rheometer, it must be taken into account that the total force $F_{total}$ is composed of:

$$F_{total} = F_{viscose} + F_{elast.} + F_{channel} + F_{KR}$$

where $F_{viscose}$=: Force that is necessary to overcome the resistance to flow in the measuring nozzle;

$F_{elast.}$=: Force for overcoming all flow losses before and after the measuring nozzle;

$F_{channel}$=: Force for the fluid transportation in the feed channel; and $F_{KR}$=: Force for overcoming the friction between the piston and the feed channel.

The composition of the total force is also shown in FIG. 1, which is a schematic view of a standardized measuring cell for determining MFR or MVR values.

The shear stress τ which can be calculated from the total force $F_{total}$ that acts upon the piston, is therefore not completely available as pressure difference, so as to overcome the resistance to flow of the measuring nozzle, since it is necessary to apply, for example, a piston force $F_{KR}$, so as to overcome the friction between the piston and the feed channel. A further component of force $F_{channel}$ is necessary for the fluid transportation in the feed channel. This force component is dependent on the filling level. Finally, a force component $F_{elast.}$ accounts for all flow losses before and after the measuring nozzle, which are caused by the elastic properties of the melt. Based on the small L/D ratio of the measuring nozzle in laboratory instruments, $F_{elast.}$ may occasionally be of as high as the actual force $F_{viscose}$, which is necessary to overcome the resistance to flow in the measuring nozzle.

From the foregoing thoughts it follows that in the stress-controlled on-line test only the shear stress $\tau_W$ is kept constant, which is caused by the force component $F_{viscose}$. This simplifying assumption may reflect only in part the substantially more complex flow conditions in the laboratory instrument. Thus, the viscose-elastic effects that can be established, for example, by the amounts of the inlet and outlet pressure losses, remain unconsidered, though these effects are reflected in the standardized MFR or MVR measurement based on the geometry of the standard measuring nozzle.

Thus, the extent to which a satisfactory concurrence of lab and on-line values is realized, is substantially dependent on the transfer models or marginal conditions that are established in these transfer models.

The MFR value can be determined from the stress-controlled, continuous capillary rheometer test as:

$$MFR_{\text{on-line}} = MFR_{\text{lab. cal.}} \cdot \frac{\gamma_{\text{on-line}}}{\gamma_{\text{cal.}}} \quad (1)$$

In this equation, it is presumed that the MFR value of the raw material $MFR_{lab,cal}$ is known and can be used to determine the corresponding shear rate $\gamma_{cal}$ in the MFR instrument, namely under standardized laboratory conditions, as:

$$\gamma_{\text{cal.}} = 1,833 \cdot \frac{MFR}{\rho} \quad (2)$$

While a constant shear stress on the wall ($\tau_W$=constant) is predetermined, product fluctuations are bound to lead to varying volume flows V. In this process, an actual shear rate $\gamma_{on-line}$ adjusts itself, which is directly proportionate to the new MFR value.

However, equation (1) allows to obtain an acceptable correspondence between computed and actually measured values only, when the molecular weight distributions of the thermoplastic materials that undergo change during the process, such as, for example, polymer charges, are approximately the same in proportion to the raw material, which is characterized by $MFR_{lab,cal}$.

According to Vinogradov and Malkin, melts with a similar molecular weight distribution are reducible to a master viscosity function that is invariant to molecular weight. Once this strict marginal condition is met, the ratio of the shear rates in equation (1) is directly proportionate to the changes of the average molecular weight $M_W$. In this case, the computed $MFR_{on-line}$ value corresponds well with the value measured in the laboratory. However, if the molecular weight distribution has changed significantly, it will be necessary to use as a basis a new calibration value $MFR*_{lab,cal}$.

Until now, it has been common practice to check the calibration value $MFR_{lab,cal}$ with reference to parallel conducted laboratory measurements again and again for its validity. On the one hand, this procedure is time consuming and, on the other hand, it also leads to inaccuracies in the determination of melt flow index values.

The condition of rheological similarity which enables a successful shift and mastering of the viscosity function, is met, among other things, when the slope of the viscosity functions in question remains constant under constant stresses. This is easy to verify in the on-line process, in that the flow exponent n is computed with two constant shear stresses, which are controlled one after the other. Another possibility is to measure the slope n of the continuously measured flow curve at constant shear rates, and to correlate same with different lineage structures of polyamides.

In a further method, a wedge gap nozzle is used to determine the flow exponent n of the viscosity spectrum that can be attained with a wedge gap nozzle, at the same time as the MFR value according to equation (1) is determined. Should the flow exponent change significantly, it can be presumed that the molecular weight distribution has changed. In this instance, it will be necessary to redetermine the calibration values. This procedure has the advantage that the flow exponent n is determined in a range of constant stress. As a result, an always constant flow behavior is present, so that the flow exponent may be rated as a significant measure for changes in the molecular weight distribution. However, if the flow exponents of different melts are compared in points of constant shear rate, it will not be possible to evaluate the slopes that are determined therein as a representative measure of changes in the molecular weight distribution, since at constant shear rates in the non-Newtonian range, the stress conditions are always different.

The present invention therefore proposes a method that facilitates an acceptable concurrence of laboratory and on-line measurements irrespective of the above-described limiting perquisites. Within the scope of this method, the model setup is also constantly examined. Necessary corrections of the adjusted values are made automatically.

As initially described, most on-line rheometers take into account only the force component $F_{viscose}$, which is needed to overcome the resistance to flow in the measuring nozzle, and which represents the viscose components of energy, since within the scope of on-line capillary rheometers measuring nozzles with a large L/D ratio are used.

However, in the determination of melt flow index values under standardized laboratory conditions, one ought not neglect the elastic energy losses, which are to be attributed to the comparatively small L/D ratio of the measuring nozzle that is used in this instance. These elastic energy losses necessitate that the shear stress $\tau_{MFR}$ computed from the selected load weight $F_{total}$ and the therewith connected shear rate $\gamma_a$ be always higher than the shear stress $\tau_{cap}$ in the capillary rheometer, which is necessary for generating the corresponding MFR value. Connected with the shear stress $\tau_{cap}$ is the shear rate $\gamma_{MFR}$. FIG. 2 shows the above-described correlation between shear rate $\gamma$ and shear stress $\tau$, which is reflected in the flow curve.

The slope of the flow curve in the range $\tau_{MFR}$–$\tau_{cap}$, thus results as:

$$\tan\alpha = \frac{\tau_{MFR} - \tau_{cap.}}{\gamma_a - \gamma_{MFR}} \quad (3)$$

After a corresponding transformation, the result is:

$$\frac{\gamma_{MFR}}{\gamma_a} = 1 - \frac{\tau_{MFR} - \tau_{cap.}}{\tan\alpha \cdot \gamma_a} \quad (4)$$

The equation (4) furnishes a stress analysis in the form of a dimensionless shear rate $\gamma^*$:

$$\gamma^* = \frac{\gamma_{MFR}}{\gamma_a} \quad (5)$$

The resultant shear stress difference $\tau_{MFR}$–$\tau_{cap}$, which can be derived from the balance of forces of the MFR melt flow indexer used under laboratory conditions, has the form:

$$\tau_{MFR} - \tau_{viscose} = \tau_{elast.} + \tau_{channel} + \tau_{leak.} \quad (6)$$

Since the energy component $\tau_{leak.}$, which must be applied for the leakage flow, can be neglected, and since the energy loss $\tau_{channel}$ is substantially smaller than the elastic inlet and outlet effects, the stress difference $\tau_{MFR}$–$\tau_{cap}$ may be denoted the elastic stress component $\tau_{elast.}$ in a first approximation. Thus, a dimensionless Weißenberg number Wb can be derived from the equation (4):

$$1 - \frac{\tau_{MFR} - \tau_{cap.}}{\tan\alpha \cdot \gamma_a} = 1 - \frac{\tau_{elast.}}{\tau_{viscose.}} = 1 - Wb \qquad (7)$$

In this equation, $\tau_{cap}$ corresponds in a first approximation to the stress $\tau_{viscose}$ according to equation (6). Thus, from equations (5) and (7), the dimensionless formula:

$$\gamma^* = 1 - Wb \qquad (8)$$

is obtained.

With equation (8) the occurring elastic and viscose stress components are correlated. The substitution of the stress difference $\tau_{MFR} - \tau_{cap}$ in the power function according to $$\tau = k \cdot \gamma^n \qquad (9)$$

where n correspond to the flow exponent and k to the consistency, results in:

$$\tau_{MFR} - \tau_{cap.} = k(\gamma^n_a - \gamma^n_{MFR}) \qquad (10)$$

Analogously to equation (7), a further transformation results:

$$\frac{\gamma_{MFR}}{\gamma_a} = \sqrt[n]{1 - \frac{\tau_{MFR} - \tau_{cap.}}{k \cdot \gamma^n_a}} = \sqrt[n]{1 - Wb} \qquad (11)$$

From the shear stress $\tau_{cap}$, it is possible to determine, after a further transformation, the pressure drop $\Delta p$ in the on-line capillary rheometer as:

$$\Delta p_{\text{on-line}} = \frac{2L}{R}[\tau_{MFR} - k(\gamma^n_a - \gamma^n_{MFR})] \qquad (12)$$

On the condition that the MFR value is known and with quasi constant viscoelastic stress conditions, the equation (12) can be used to determine a desired value input for the pressure drop $\Delta p_{\text{on-line}}$ in the capillary rheometer. This pressure drop $\Delta_{\text{on-line}}$ leads to a volume flow V through the measuring nozzle, from which it is possible to compute the actual shear rate $\gamma_{\text{on-line}}$ and, thus, in turn the MFR value according to equation 2.

In the case of an existing MFR function for is all stress stages i and the corresponding power function $$\tau = k_i \gamma^i_{MFR} \qquad (13)$$

the general pressure equation is obtained for the on-line capillary rheometer with equation (11)

$$\Delta p_{\text{on-line}} = \frac{2L}{R}\left\{\tau_{MFR}\left[\tau_{MFR}\left(1 - \frac{\sqrt[i \cdot n]{\frac{\tau_{MFR}}{k_i}}}{\frac{\tau_{MFR}}{k}}\right)\right]\right\} \qquad (14)$$

A change in the viscoelastic stress conditions is reflected in a considerable change of the. Weißenberg term. In this instance, it is necessary to replace the stress difference $\tau_{MFR-\tau Cap}$ of equation (11) with expressions that are independent of each other. The elastic inlet and outlet pressure losses $\tau_{elast.}$ of equation (6) can be directly characterized by the Bagley term $p_C$, which is to be determined at the shear rate $\gamma_{MFR}$. Thus, $$\tau_{elast.} = p_{c|\dot\gamma_{MFR}} \cdot \left(\frac{R}{2L}\right)_{MFR} \qquad (16)$$

Based on the pressure conditions in the melt flow indexer used in the laboratory, a shear rate $\gamma_{channel}$ is obtained in the channel, which is approximately 100 times smaller than the shear rate in the measuring nozzle:

$$\gamma_{channel} = 0.01063 \cdot \gamma_{MFR} \qquad (17)$$

For many polymers, the range of the Newtonian limiting viscosity $\eta_O$ is reached at the shear rate $\gamma_{channel}$. The influence of the filling level on the MFR value measured in the laboratory instrument is taken into account by the term $L_Z(1)/L_Z$. Thus, the energy component that must be applied for $\tau_{channel}$ can be determined as follows:

$$\tau_{channel} = 0{,}011063 \cdot \eta_0 \cdot \gamma_{MFR} \cdot \frac{L_z(t)}{L_z} \qquad (18)$$

The essential stress losses that may occur during the melt flow index measurement, are thus known. This allows to redefine equation (11):

$$\frac{\gamma_{MFR}}{\gamma_a} = \sqrt[n]{1 - \frac{p_{c|\dot\gamma_{MFR}} \cdot \left(\frac{R}{2L}\right)_{MFR}}{k \cdot \gamma^n_a} + \frac{0{,}01063 \cdot \eta_0 \cdot \gamma_{MFR}}{k \cdot \gamma^n_a} \cdot \frac{L_z(t)}{L_z}} \qquad (19)$$

The only unknown quantity in equation (19) is $\gamma_{MFR}$, which can now be determined by the iterative method. With that, also the actual melt flow index MFR of equation (2) is determined. FIG. 3 shows the corresponding algorithm for an on-line capillary rheometer, which allows to determine continuously the flow properties of a melt and to evaluate same in the form of MFR values. In this process, the measuring conditions, namely $\Delta p$ and, thus, likewise the actual evaluation of the measurement are adapted to possible changes in the viscoelastic behavior of the melt.

The practical use of the claimed and above-derived algorithm is described in more detail within the scope of the description of the Figures, in particular with reference to FIG. 3.

The above-described algorithm of a self-correcting on-line control loop requires a determination of the viscosity function under at least two different stress conditions, so as to be able to determine the flow exponent n continuously.

Moreover, in the event that the viscoelastic behavior of the melt being examined changes significantly, so that the term (1-WB) remains no longer constant, it will be necessary to determine likewise the Bagley term.

Normally, in on-line rheometers, the viscosity function is determined by inputting different shear rates or different shear stresses. To this end, the individual stationary shear rates or shear stresses are successively input with a shift in time. This time-consuming determination of the viscosity function contradicts the real time requirements of an on-line rheometer, whose duty is to perform process-attendant measurements under real time conditions.

For this reason, it has been common practice in the past to use on-line rheometers with at least two measuring nozzles of different geometry. With that, it is possible to cover a range of the viscosity function at a constant volume throughput or constant pressure difference. Likewise known is the use of on-line rheometers with two serially connected nozzles, whose L/D ratio ranges from 3 to 30. In this instance, it is likewise possible to cover a corresponding range of the viscosity function at a predetermined constant volume throughput.

In a further variant, four serially connected nozzles with a constant L/D ratio are used, so as to cover at a predetermined constant volume flow a largest possible range of the viscosity function. In accordance with a similar concept, nozzles with different diameters are connected parallel and supplied with identical volume flows. To eliminate elastic inlet effects, it is also possible to use two serially connected nozzles with identical diameters, but different lengths.

An advantageous variant of the method in accordance with the invention provides for the use of two parallel connected nozzles, whose L/D ratio ranges from 10 to 30. Furthermore, a melt pump is provided, which allows to divide the melt being delivered into two independent and quantitatively different volume flows. In this instance, the melt pump could be, for example, a gear pump. The ratio of the two volume flows should be in the range of 1/10. A possible division of the total volume flow $V_{total}$ provides for the following qualitative ratio:

$$V_{total} \geq V_A \geq \geq \geq V_B \quad (20)$$

This results in a degree of delivery X for the connected volume flows $V_A$ and $V_B$ according to:

$$V_{total} = V_{A(1-X)} + V_{B(X)} \quad (21)$$

with: $0.1 \leq X \leq 1$

With the aid of the volume flows $V_{A(1-X)}$ and $V_{B(X)}$ in combination with the two parallel connected nozzles of the on-line capillary rheometer, it possible to determine a viscosity spectrum with a constant parameter input, which may proceed either pressure-controlled or speed-controlled. From this, it is also possible to determine the flow exponent n and the consistency k. Thus, in this instance, the determination of the viscosity function is continuous in the continuous operation.

To examine the viscoelastic basic adjustment, a volume flow $V_C$ is input in a short-time operation. This volume flow requires that temporarily a constant shear rate be attained in both nozzles:

$$\gamma_A = \gamma_B \quad (22)$$

Since the two nozzles are of different lengths, it is now possible to compute the Bagley term $P_C$. While equation (22) is a compromise with respect to the classic determination of the Bagley term, which requires constant nozzle radii, the only possible source of error, according to which a sliding of the melt along the capillary wall could adversely affect the computation of the inlet pressure losses, is to be excluded at the relatively low shear rates $\gamma_{MFR}$.

Based on the measured data requirements of the method in accordance with the invention, the following configurations of a two-nozzle system are proposed:

1. $V_A = V_B$ as well as $d_1 = d_2$.
Nozzles $D_1$ and $D_2$ with constant diameters $d_1$ and $d_2$ and different lengths $L_1$ and $L_2$ receive parallel advancing volume flows $V_A = V_B$. Thus, $\gamma_A = \gamma_B$ is met. For a short period of time, a volume flow $V_C$ is input, where: $V_C \neq (V_A, V_B)$; this leads to: $\gamma_A \neq \gamma_B$.

2. $V_A = V_B$ as well as $d_1 \neq d_2$.
Nozzles $D_1$ and $D_2$ with different diameters $d_1$ and $d_2$ and different lengths $L_1$ and $L_2$ receive parallel advancing volume flows $V_A = V_B$. Thus, $\gamma_A \neq \gamma_B$ is met. For a short period of time a volume flow $V_C$ is input, which is to result in that: $\gamma_A = \gamma_B$ is met.

3. $V_A \neq V_B$ as well as $d_1 = d_2$.
Nozzles $D_1$ and $D_2$ with constant diameters $d_1$ and $d_2$ and different lengths $L_1$ and $L_2$ receive parallel advancing volume flows $V_A \neq V_B$. Thus, $\gamma_A \neq \gamma_B$ is met. For a short period of time a volume flow $V_C$ is input, which is to result in that: $\gamma_A = \gamma_B$ is met.

4. $V_A \neq V_B$ as well as $d_1 \neq d_2$.
Nozzles $D_1$ and $D_2$ with different diameters $d_1$ and $d_2$ and different lengths $L_1$ and $L_2$ receive parallel advancing volume flows $V_A \neq V_B$. Thus, $\gamma_A \neq \gamma_B$ is met. For a short period of time a volume flow $V_C$ is input, which is to result in that: $\gamma_A = \gamma_B$ is met.

In conjunction with the Figures, the following describes the method of the present invention as well as a variant of an on-line capillary rheometer, which can be used in an especially advantageous manner within the scope of the method in accordance with the invention.

Figure 1:
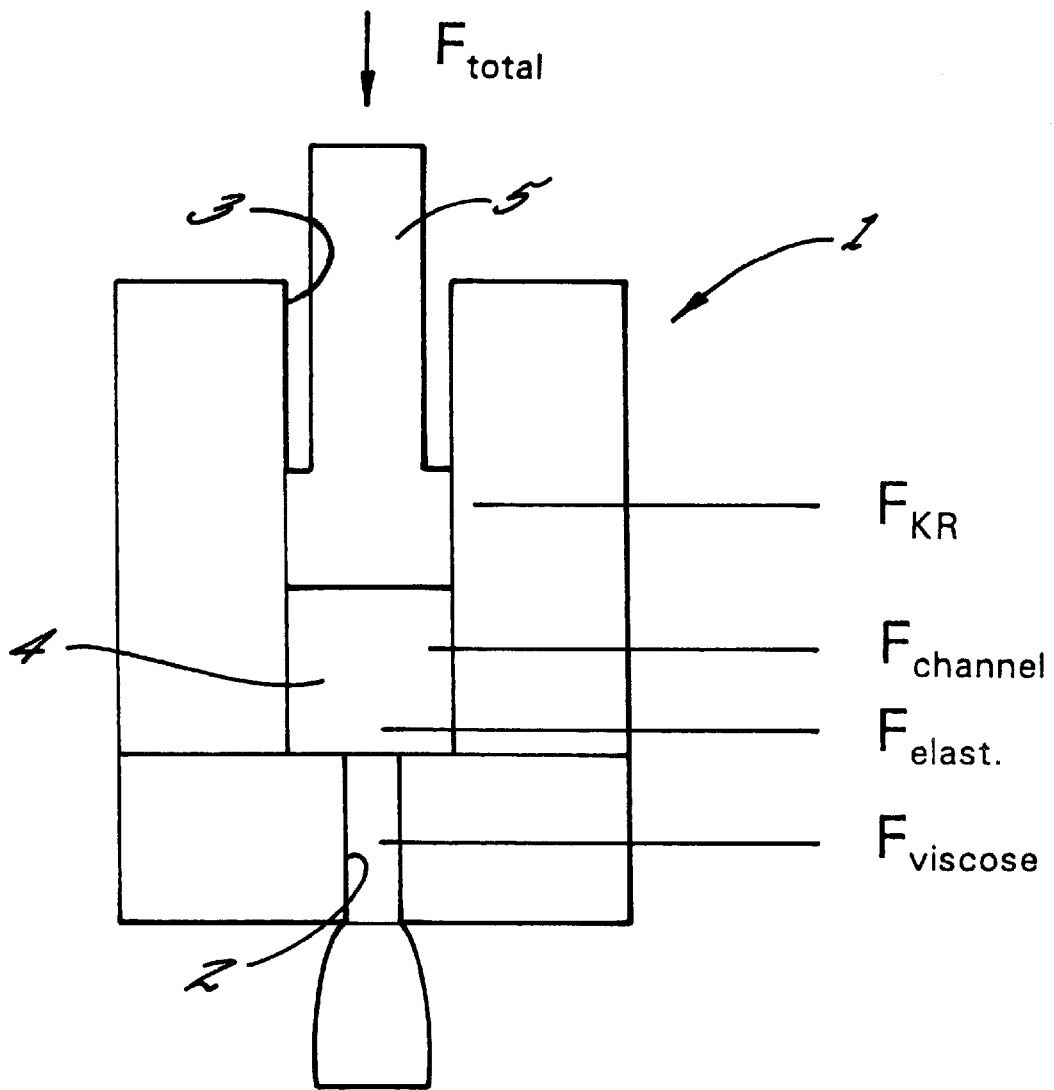
FIG. 1 is a schematic view of the construction of a melt flow indexer (MFR instrument) and serves to illustrate the balance of forces as exists in such an instrument.

FIG. 1 is at least a schematic view of a measuring cell 1 of a laboratory instrument, which is used to determine melt flow index values under standardized laboratory conditions. An important component of the measuring cell 1 is a measuring nozzle or measuring capillary 2, which receives via a feed channel 3 a melt 4 that is to be tested. To this end, the melt 4 is subjected to a defined load force. This occurs by means of a piston 5 that acts upon the melt 4 in feed channel 3.

When determining the melt index according to DIN, ISO, the measuring nozzle 2 and, if need be, also the feed channel 3 are temperature controlled. The measuring nozzle 2 has a diameter of 2.1 mm and is 8 mm long. The load weight is selected as a function of the melt being tested, and ranges from 2.16 kg to 21.6 kg.

The total force $F_{total}$ that weighs upon the piston 5 is distributed over several force components, which is indicated in FIG. 1.

$$F_{total} = F_{viscose} + F_{elast.} + F_{Channel} + F_{KR}$$

Thus, the total force $F_{total}$ is available only in part, namely with force component $F_{viscose}$, for overcoming the resistance to flow in the measuring nozzle 2. In addition, it is also necessary to apply a force component $F_{KR}$, so as to overcome the friction between piston 5 and feed channel 3. Furthermore, a force component $F_{Channel}$ is needed for the fluid advance in feed channel 3. This force is again dependent on the filling level of the melt 4 in feed channel 3. Finally, yet another force component $F_{elast.}$ accounts for flow losses before and after the measuring nozzle 2, which are caused by the elastic properties of the melt. In the illustrated case of a laboratory instrument, the force component $F_{elast.}$ may occasionally be as high as the force component $F_{viscose}$, which is necessary to overcome the resistance to flow in the measuring nozzle.

Figure 2:
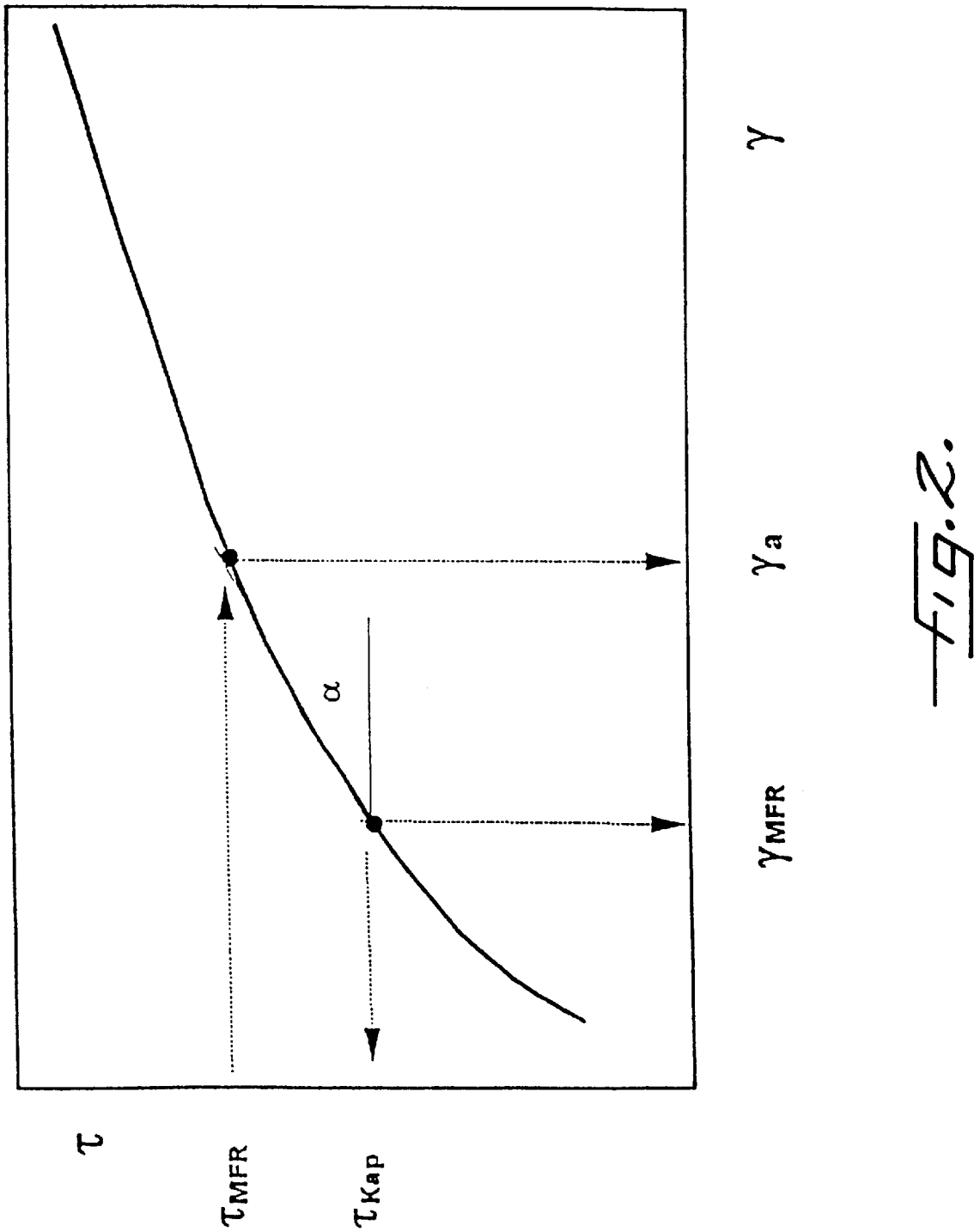
FIG. 2 illustrates a flow curve with the shear stress ratios computed for a predetermined melt index value and the corresponding shear stress ratios that actually exist in an on-line capillary rheometer.

From the balance of forces as shown in FIG. 1 and as exists in a laboratory instrument, it follows that a shear stress $\tau_{MFR}$ which is computed from the total force $F_{total}$ that acts upon the piston, and the therewith connected shear rate $\gamma_a$ are always higher than the shear stress $\tau_{Cap}$ in the capillary rheometer, which is necessary to generate the corresponding MFR value. This is due to the different L/D ratios on the one hand on the measuring nozzle of a laboratory instrument and on the other hand on the measuring nozzle of a capillary rheometer. Based on the different geometries, the elastic energy losses are normally substantially lower, when measuring the melt flow index with a capillary rheometer, than in the determination of the melt index with the aid of a laboratory instrument. The correlation between the shear stress ratios in an on-line capillary rheometer and in a laboratory instrument is illustrated by a flow curve shown in FIG. 2.

Table 1 shows results of tests which were conducted in connection with equation (12). For a series of polypropylene charges in an MFR range from 1 to 6 g/10 min., a necessary predetermined pressure $\Delta p_{1-Wb}$ was computed by equation (12). Table 1 also shows the experimentally determined control pressure $\Delta p_{on-line\ exp.}$. With the exception of the last charge, deviations were found between the computed and the experimental values, which were below 5%.

A comparable result was obtained from the computations for known LDPE and HDPE samples in Table 2. The greatest deviations were between 4% (1800 S) and 6% (1840 S).

The trend is that deviations between experiment and computation are greater, the smaller the Weißenberg term (1-Wb). A decrease of (1-Wb) normally leads to an increase of the elastic stress component. For the accuracy in determining equation (11), the exact computation of the flow exponent n is of greatest importance. Basically, it can be assumed that for charges, whose computed Weißenberg terms remain constant, the stress ratio $\tau_{MFR}$-$\tau_{Cap}$ will also remain unchanged. In this case, it is also possible to maintain the original calibration with $MFR_{lab,cal}$ according to equation (1).

Table 2 illustrates that the (1-Wb) terms of the PE types can be divided into two groups, namely a group with $(1-Wb)_A=0.61\pm0.05$, and a group $(1-Wb)_B=0.74\pm0.05$. A product change within respective limits is possible without recalibration.

However, if in a change of the charge the term (1-Wb) changes significantly, such as, for example, in a change from 3200 K to 1810 D, it will have to be assumed that also the shear stress ratio $\tau_{elast}/\tau_{viscose}$ has changed. In this instance, a recalibration would therefore be necessary.

Figure 3:
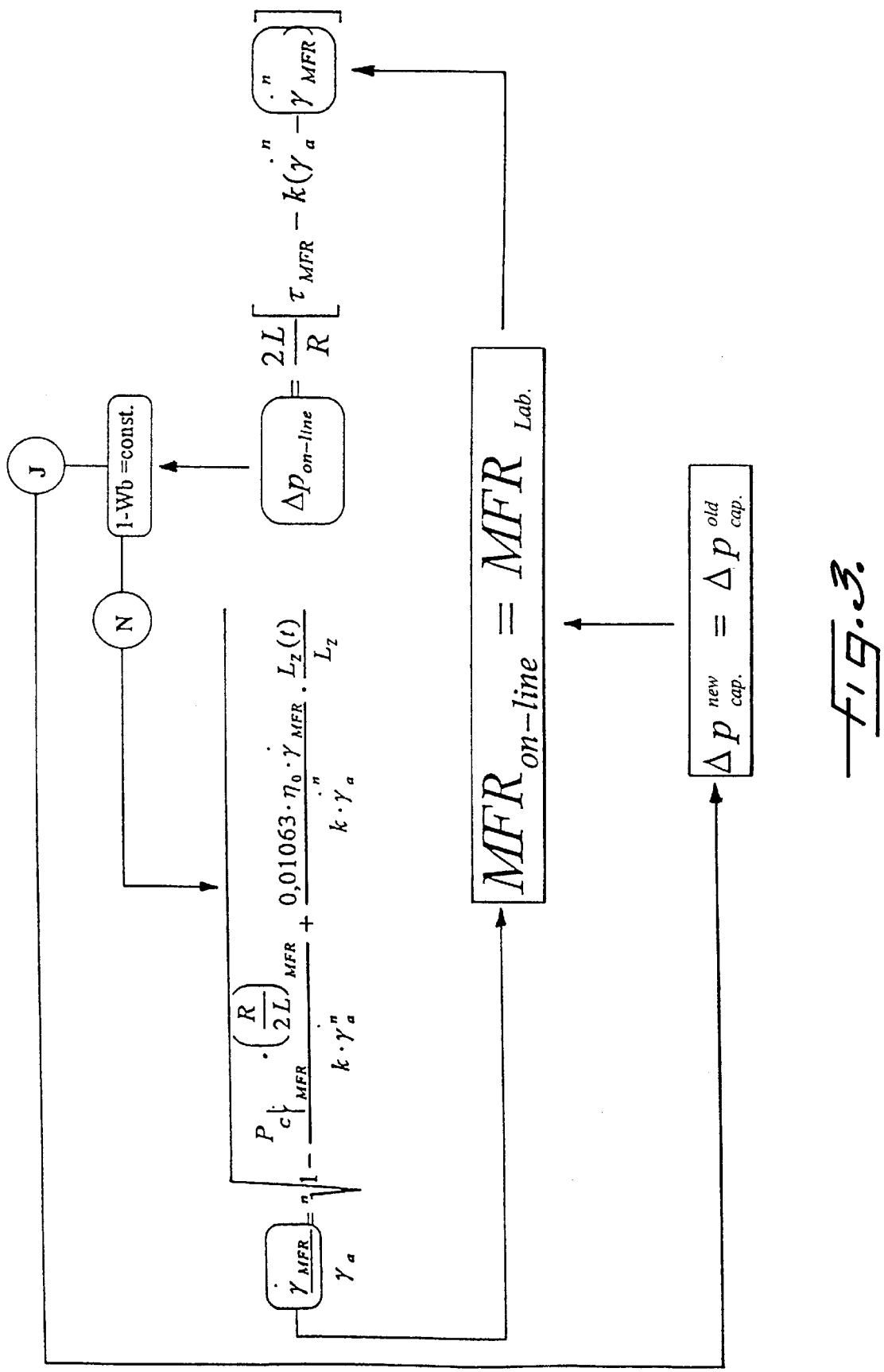
FIG. 3 illustrates a flow diagram of an algorithm applied within the scope of the method in accordance with the invention.

FIG. 3 shows the algorithm underlying the method of the present invention, which facilitates an on-line determination of melt flow index values even with consideration of viscoelastic stress changes.

To enter into this control loop, it is necessary that the melt index value $MFR_{Lab}$ of the product being tested be known as a start allowance. With the determination of the viscosity function in the range of the shear rate $\gamma_{MFR}$, is then possible to compute the desired pressure input as $\Delta p_{on-line}$ by equation (12). Since at the beginning of the measurements, no comparison value exists for the term $(1-Wb)^{1/n}$, $\Delta p_{on-line}$ according to equation (1) will furnish a computed MFR value, which corresponds within an acceptable tolerance to the laboratory value. As long as the continuous determination of the Weißenberg expression remains constant within limits, one can assume that the desired value for $\Delta p_{on-line}$ will bring good results and, thus, can be maintained.

However, if the viscoelastic behavior of the actual condition of the melt changes in a manner that the stress ratio of the viscose and elastic stress components remains no longer constant, it will be necessary to directly compute the expression $\tau_{MFR}$-$\tau_{Cap}$ with the aid of equation (19). Thus, it is possible to directly determine the actual shear rate $\gamma^*_{MFR}$, which would adjust itself in the laboratory instrument. From this again the actual MFR value will be obtained. At $\gamma^*_{MFR}$, equation (12) results in a new desired pressure $\Delta p_{on-line}$, which considers the changed viscoelastic condition of the melt, and which ensures that the on-line measurement and the laboratory value of the MFR correspond within acceptable limits.

Thus, a closed control loop is present, which determines in a continuous operation a significant range of the viscosity function and checks in addition the viscoelastic properties of the melt, so as to create the basis for a determination of the MFR in conformity with the process time.

Figure 4:
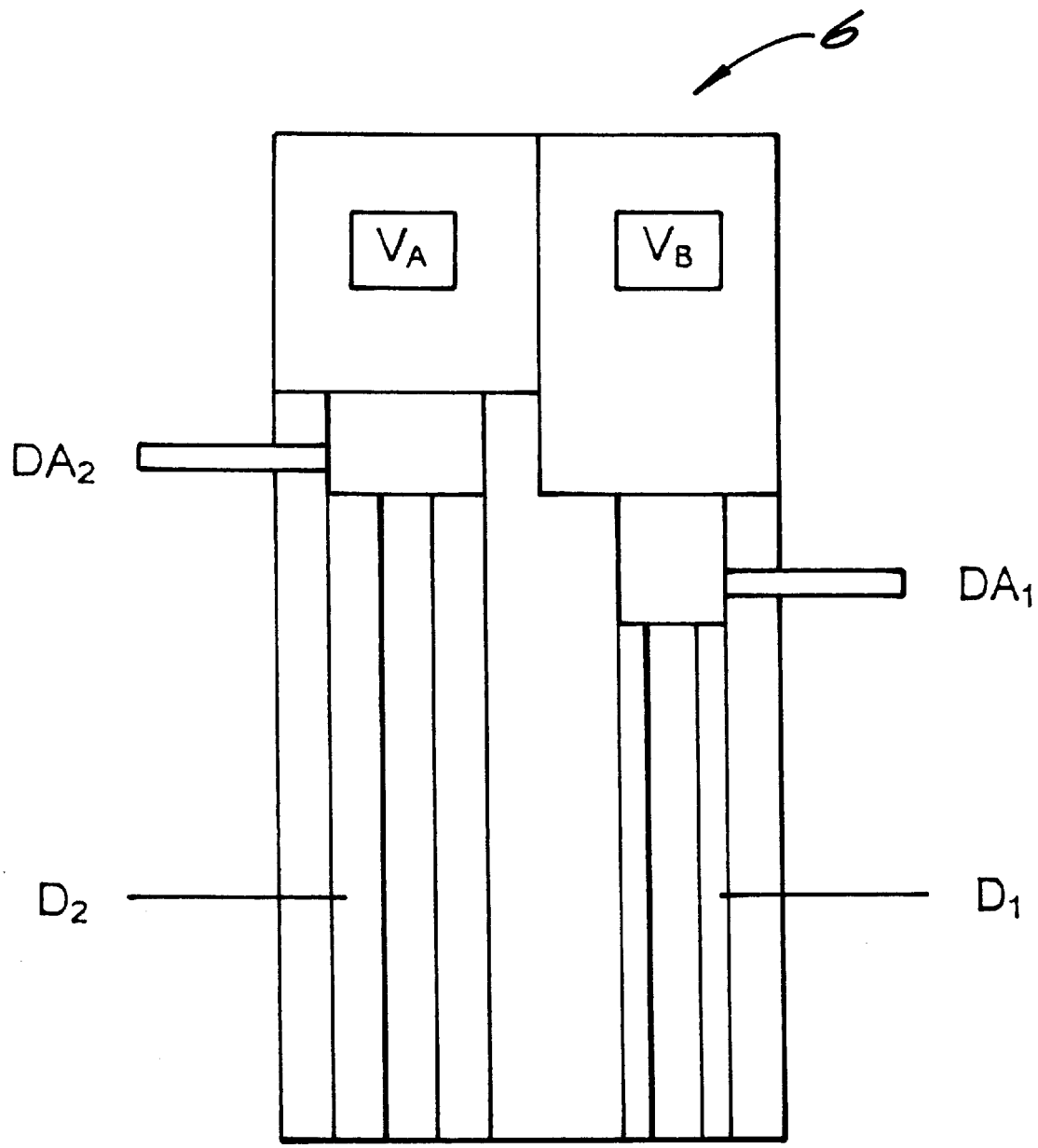
FIG. 4 illustrates a measuring cell of an on-line capillary rheometer with two parallel extending capillaries or measuring nozzles of different lengths, which receive different volume flows.

FIG. 4 illustrates a measuring cell 6 of an on-line capillary rheometer, which is particularly well suited for carrying out the method of the present invention. The measuring cell 6 comprises as measuring nozzles two parallel extending capillaries D1 and D2. The capillaries D1 and D2 have different lengths, and they receive simultaneously different volume flows $V_A$ and $V_B$. The pressure drop that occurs at the respective measuring nozzle D1 or D2 is detected by correspondingly arranged pressure gauges DA1 and DA2.

Figure 5:
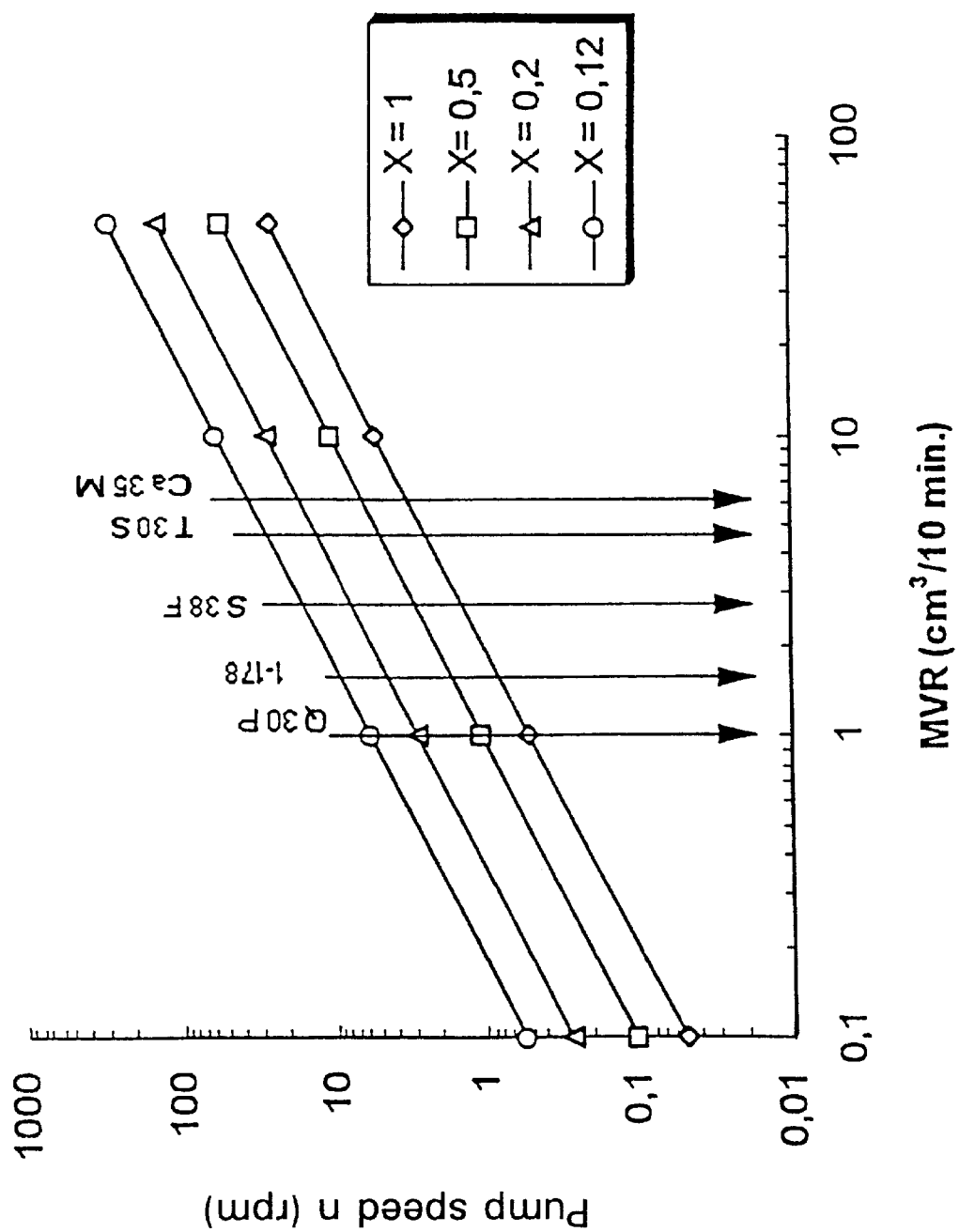
FIG. 5 illustrates the rotational speed range of a melt pump as a function of MVR with different curves of the pump capacity, when a nozzle with an L/D ratio of 60/4 is used.

Finally, FIG. 5 illustrates the capacity curve of a spin pump for the volume flow $V_B$ (X) as a function of different delivery capacity factors X for the known PP melts. For the melt with curve X=1 and a nozzle of 60/4, for example, a rotational speed range of approximately 0.4 to 2 rpm is obtained. Rotational speed adjustments below 1 rpm are extremely critical. In case of the described polymers, one would have arrived at the boundary range of the rheometer layout.

If, for example, in the layout of the pump for volume flow $V_B$, a delivery characteristic according to curve X=0.2 is provided, the rotational speed range will increase as a whole by about ten times. Only this facilitates the conditions of a reproducible and reliable adjustment of the melt pump for the polymer range under discussion.

TABLEA 4.1

| Material PP | MVR Lab | $\Delta\rho$ on-line, Exp. | MVR on-line, Exp. | $\Delta\rho(1-Wb)^{1/n}$ | $\Delta\rho$ Exp $-\Delta\rho(1-Wb)^{1/n}$ $\Delta$ % | 1-Wb $M_{0=2.16\ kg}$ |
|---|---|---|---|---|---|---|
| S 38F | 2.74 | 9.63 | 2.75 | 9.68 | −0.52 | 0.82 |
| T 30S | 4.69 | 9.62 | 4.67 | 9.66 | −0.42 | 0.82 |
| 1-178 | 1.39 | 9.21 | 1.39 | 9.58 | −4.02 | 0.81 |
| Ca 35M | 5.89 | 9.71 | 5.9 | 9.91 | −2.06 | 0.84 |

TABLEA 4.1-continued

| Material PP | MVR Lab | Δρ on-line, Exp. | MVR on-line, Exp. | $\Delta\rho(1 - Wb)^{1/n}$ | $\dfrac{\Delta\rho\ \text{Exp} - \Delta\rho(1-Wb)^{1/n}}{\Delta}$ % | 1-Wb $M_{0=2.16\ kg}$ |
|---|---|---|---|---|---|---|
| Q 30 P | 1.09 | 9.2 | 1.04 | 7.74 | 15.9 | 0.66 |

Computed and experimentally determined desired pressure values for the continuous stress-controlled MFR measurement of different polypropylene types.

TABLEA 4.2

| MATERIAL PE | MVR Lab | ΔρRTR Exp. | $\Delta\rho(1-Wb)^{1/n}$ | $\dfrac{\Delta\rho\ \text{Exp} - \Delta\rho(1-Wb)^{1/n}}{\Delta\rho}$ % | 1-Wb | Category $M_{0-2.16\ kg}$ |
|---|---|---|---|---|---|---|
| 1800 S | 23.9 | 8.8 | 8.4 | 3.7 | 0.72 | A |
| 2420 K | 5.2 | 7.9 | 7.8 | 1.3 | 0.66 | A |
| 1810 D | 0.31 | 5.7 | 5.5 | 3.5 | 0.59 | A |
| 3020 K | 4.8 | 8.9 | 8.7 | 2.3 | 0.74 | B |
| 1800 H | 1.8 | 7.8 | 7.8 | 0 | 0.66 | A |
| 2420 F | 0.96 | 7.2 | 7.3 | −1.4 | 0.78 | B |
| 1812 E | 0.64 | 6.6 | 6.5 | 1.5 | 0.69 | B |
| 1840 D | 0.3 | 5.0 | 4.7 | 5.6 | 0.5 | |
| 6021 D | 0.3 | 5.2–5.5 | 5.4 | 0 | 0.58 | A |
| 5021 D | 0.27 | 5.2 | 5.2 | 0 | 0.56 | A |

Computed and experimentally determined desired pressure values for the continuous stress-controlled MRF measurement of polyethylene.

I claim:

1. Method of determining and evaluating melt flow index values (MFR values) of thermoplastic materials with the aid of a continuously operating on-line capillary rheometer, wherein a pressure difference Δp between an inlet and outlet of a measuring nozzle of the capillary rheometer is predetermined, and Δp is adjusted such that $$MFR_{on\text{-}line} = MFR_{lab},$$

where $MFR_{on\text{-}line}$ is the melt flow index value that is determined on line, and $MFR_{lab}$ the melt flow index value that is determined under standardized laboratory conditions, characterized in that a desired value input for the pressure drop Δp in the capillary rheometer is determined as $$\Delta p_{\text{on-line}} = \frac{2L}{R}[\tau_{MFR} - k(\gamma_a^n - \gamma_{MFR}^n)]$$

and is not varied as long as a continuously determined ratio of an elastic stress component $\tau_{elast.}$ to a viscose stress component $\tau_{viscose}$ of the shear stress $\tau_{MFR}$ does not change significantly, where L=: Length of the measuring nozzle;
R=: Radius of the measuring nozzle;
$\tau_{MFR}$=: Computed shear stress for MFR under standardized laboratory conditions;
k=: Consistency
$\gamma_a$=: Computed shear rate for MFR under standardized laboratory conditions; $\gamma_{MFR}$=: Existing shear rate of the MFR in the on-line capillary rheometer; and
n=: Flow exponent.

2. Method of claim 1, characterized in that the ratio of the elastic to the viscose stress component of the shear stress is determined as $$\frac{\gamma_{MFR}}{\gamma_a} = 1 - \frac{\tau_{MFR} - \tau_{cap.}}{\tan\alpha \cdot \gamma_a} = 1 - \frac{\tau_{elast.}}{\tau_{viscose}} = 1 - Wb$$

where $\tau_{Cap}$=: Shear stress in the capillary rheometer for producing the MFR;
tanα=: Slope of the flow curve in the range $\tau_{MFR}-\tau_{Cap}$;
Wb=: Dimensionless Weißenberg number.

3. Method of claim 2, characterized in that the ratio of the elastic to the viscose stress component of the shear stress is newly determined as $$\frac{\gamma_{MFR}}{\gamma_a} = \sqrt[n]{1 - \frac{p_{C}|\gamma_{MFR} \cdot \left(\frac{R}{2L}\right)_{MFR}}{k \cdot \gamma_a^n} + \frac{0,01063 \cdot \eta_0 \cdot \gamma_{MFR}}{k \cdot \gamma_a^n} \cdot \frac{L_z(t)}{L_z}}$$

when the ratio that is continuously determined as $$\frac{\gamma_{MFR}}{\gamma_a} = 1 - \frac{\tau_{MFR} - \tau_{cap.}}{\tan\alpha \cdot \gamma_a} = 1 - \frac{\tau_{elast.}}{\tau_{viscose}} = 1 - Wb$$

between the elastic stress component $\tau_{elast.}$ and the viscose stress component $\tau_{viscose}$ of the shear stress $\tau_{MFR}$ has changed significantly, where $p_C|\gamma_{MFR}$=: Bagley term determined at the shear rate $\gamma^*_{MFR}$;
$\eta_O$=: Newtonian limiting viscosity;
$L_Z(t)L_Z$=: Influence of the filling level on the MFR measured under standardized laboratory conditions, and that the thus newly determined ratio between the elastic and the viscose stress component of the shear stress serves as a new reference value for subsequent measurements.

4. Method of claim 3, characterized in that Δp is newly determined as $$\Delta p_{\text{on-line}} = \frac{2L}{R}[\tau_{MFR} - k(\gamma_a^n - \gamma_{MFR}^n)]$$

as soon as the continuously determined ratio between the elastic stress component $\tau_{elast.}$ and the viscose stress component $\tau_{viscose}$ of the shear stress $\tau_{MFR}$ deviates substantially from the determined reference value.

5. Method of claim 1, characterized in that at the beginning of the on-line measurements the melt flow index value $MFR_{lab}$ of the thermoplastic material being monitored and the viscosity function in the range $\gamma_{MFR}$ are determined, and that thus a first desired pressure value input is determined as $$\Delta p_{\text{on-line}} = \frac{2L}{R}[\tau_{MFR} - k(\gamma_a^n - \gamma_{MFR}^n)]$$

6. Method of claim 1, characterized in that an on-line capillary rheometer with two parallel extending measuring nozzles (D1, D2) and a pump for delivering the thermoplastic material are used, the measuring nozzles (D1, D2) having each a length/diameter (L/D) ratio in the range from 10 to 30, and the pump dividing the thermoplastic material into two independent and quantitatively different volume flows (VA, VB), so that the ratio of the volume flows (VA/VB) is in a range of 1/10.

7. Method of claim 6, characterized in that the two nozzles (D1, D2) have the same diameter (d1=d2), but different lengths (L1, L2), and that the two nozzles (D1, D2) receive identical volume flows (VA=VB).

8. Method of claim 6, characterized in that the two nozzles (D1, D2) have different diameters (d1, d2) and different lengths (L1, L2), and that the two nozzles (D1, D2) receive identical volume flows (VA=VB).

9. Method of claim 6, characterized in that the two nozzles (D1, D2) have the same diameter (d1=d2), but different lengths (L1, L2), and that the two nozzles (D1, D2) receive different volume flows (VA, VB).

10. Method of claim 6, characterized in that the two nozzles (D1, D2) have different diameters (d1, d2) and different lengths (L1, L2), and that the two nozzles (D1, D2) receive different volume flows (VA, VB).

* * * * *